United States Patent
Arle et al.

(10) Patent No.: US 8,346,366 B2
(45) Date of Patent: Jan. 1, 2013

(54) SPINAL CORD IMPLANT SYSTEMS AND METHODS

(75) Inventors: Jeffrey Edward Arle, Concord, MA (US); Jay Lawrence Shils, Reading, MA (US)

(73) Assignee: Lahey Clinic Foundation, Inc., Burlington, MA (US)

( * ) Notice: Subject to any disclaimer, the term of this patent is extended or adjusted under 35 U.S.C. 154(b) by 125 days.

(21) Appl. No.: 13/071,327

(22) Filed: Mar. 24, 2011

(65) Prior Publication Data

US 2011/0224755 A1    Sep. 15, 2011

Related U.S. Application Data

(63) Continuation of application No. 12/009,176, filed on Jan. 17, 2008, now abandoned.

(60) Provisional application No. 60/881,056, filed on Jan. 17, 2007.

(51) Int. Cl.
*A61N 1/18* (2006.01)

(52) U.S. Cl. ............ 607/48; 607/49; 607/50; 607/52; 607/117

(58) Field of Classification Search .............. 607/48, 607/49, 50, 52, 117
See application file for complete search history.

(56) References Cited

U.S. PATENT DOCUMENTS

| | | | |
|---|---|---|---|
| 5,002,053 A * | 3/1991 | Garcia-Rill et al. | ............ 607/49 |
| 5,081,990 A | 1/1992 | Deletis | |
| 6,516,227 B1 | 2/2003 | Meadows et al. | |
| 6,836,684 B1 | 12/2004 | Rijkhoff et al. | |
| 6,839,594 B2 * | 1/2005 | Cohen et al. | ............ 607/48 |
| 7,610,096 B2 * | 10/2009 | McDonald, III | ............ 607/48 |
| 7,783,360 B2 * | 8/2010 | Zdravkovic et al. | ............ 607/62 |
| 2005/0246004 A1 | 11/2005 | Cameron et al. | |

OTHER PUBLICATIONS

Borisoff, et al., "Detection and Classification of Sensory Information From Acute Spinal Cord Recordings," IEEE Transactions on Biomedical Engineering, 53:81715-81719 (2006).
Coulombe, et al., "A Power Efficient Electronic Implant for a Visual Cortical Neuroprosthesis," Artificial Organs, 29(3): 233-238 (2005).
Guevremont, et al., "Locomotor-Related Networks in the Lumbosacral Enlargement of the Adult Spinal Cat: Activation Through Intraspinal Microstimulation," IEEE Transactions on Rehabilitation Engineering, 14:3266-3271.
Jilge, et al., "Initiating extension of the lower limbs in subjects with complete spinal cord injury by epidural lumbar cord stimulation," Exp Brain Res 154: 308-326 (2004).

(Continued)

*Primary Examiner* — Carl H Layno
*Assistant Examiner* — Natasha Patel
(74) *Attorney, Agent, or Firm* — Foley & Lardner LLP; Michel Morency

(57) ABSTRACT

A system for transferring spinal cord signals comprises a superior electrode and an inferior electrode. The superior electrode interfaces with a first portion of a spinal cord of a human body; and the inferior electrode interfaces with a second portion of the spinal cord. The superior electrode has at least one superior contact for receiving signals from the first portion of the spinal cord to transmit to the inferior electrode; and the inferior electrode has at least one inferior contact for transmitting signals received from the superior electrode to the second portion of the spinal cord.

13 Claims, 17 Drawing Sheets

OTHER PUBLICATIONS

McCrerry, et al., "Arrays for Chronic Functional Microstimulation of the Lumbosacral Spinal Cord," IEEE Transactions on Neural Systems and Rehabilitation Engineering, 12:2 195-207:(2004).

Minassian, et al., "Stepping-like movements in humans with complete spinal cord injury induced by epidural stimulation of the lumbar cord: electromyographic study of compound muscle action potentials," Spinal Cord 42: 401-416 (2004).

Patton and Amassian, "Single- and Multiple-Unit Analysis of Cortical Stage of Pyramidal Tract Activation," Department of Physiology and Biophysics, University of Washington School of Medicine, Seattle 5, Washington.

Pikov and McCreery, "Mapping of Spinal Cord Circuits Controlling the Bladder and External Urethral Sphincter Functions in the Rabbit," Neurourology and Urodynamics, 23:172-179 (2004).

Pinter, et al., "Epidural electrical stimulation of posterior structures of the human lumbosacral cord: 3. Control of spasticity," Spinal Cord 38: 524-531 (2000).

Sahin, M. "Information Capacity of the Corticospinal Tract Recordings as a Neural Interface," Annals of Biomedical Engineering, 32:6823-830 (2004).

Saigal, et al., "Intraspinal Microstimulation Generates Functional Movements After Spinal-Cord Injury," IEEE Transactions on Neural Systems and Rehabilitation Engineering, 12:4430-440 (2004).

Tai, et al., "Isometric Torque About the Knee Joint Generated by Microstimulation of the Cat L6 Soinal Cord," IEEE Transactions on Rehabilitation Engineering, 7:1 46-55 (1999).

Tai, et al., "Multi-joint movement of the cat hindlimb evoked by microstimulation of the lumbosacral spinal cord," Experimental Neurology, 183: 620-627 (2003).

Troyk, et al., "A Model for Intracortical Visual Prosthesis Research," Artificial Organs, 27(11): 1005-1015 (2003).

* cited by examiner

SPINAL CORD IMPLANT SYSTEMS AND METHODS

CROSS-REFERENCE TO RELATED APPLICATIONS

This application is a continuation of U.S. application Ser. No. 12/009,176, which was filed on Jan. 17, 2008, and claims the benefit of U.S. Provisional Patent Application No. 60/881,056 filed on Jan. 17, 2007, each the entirety of which is incorporated by reference herein in its entirety.

BACKGROUND

Neural interfaces have emerged as possible interventions to reduce the burden associated with some neurological diseases, injuries, and disabilities, such as spinal cord injuries which can cause reduced sensation and mobility by damaging the nerve pathways between the brain and the rest of the body. Many neural interfaces take advantage of cortical plasticity, which is the brain's ability to reorganize its functions and their locations within the brain in response to chronic changes in the received sensory information.

Researchers have considered implanting electrode devices to detect nerve signals or stimulate nerves. For example, signals detected in the brain or peripheral nervous system may be used to help control devices outside the body, such as cursors on a computer screen or prostheses; cochlear implants for the deaf stimulate auditory nerves in response to sounds; and stimulation of the spinal cord has been considered for restoring genitourinary and bowel motor functions. Studies of spinal cord recording include:

Borisoff J. F., McPhail L. T., Saunders J. T., Birch G. E., Ramer M. S., *Detection and classification of sensory information from acute spinal cord recordings*. IEEE Transactions on Biomedical Engineering. 53(8):1715-9, 2006.

Sahin M., *Information capacity of the corticospinal tract recordings as a neural interface*. Annals of Biomedical Engineering. 32(6):823-30, 2004.

Patton H. D. and Amassian V. E., *Single and multi unit analysis of cortical stage of pyramidal tract activation*. Journal of Neurophysiology. 17:345-63, 1954.

For persons suffering from paralysis due to spinal cord injury, attempts to restore motor function have relied on retraining any undamaged nerve pathways and stimulating nerves with signals generated independently of brain signals. Studies of spinal cord stimulation include:

Philip Troyk, Martin Bak, Joshua Berg, David Bradley, Stuart Cogan, Robert Erickson, Conrad Kufta, Douglas McCreery, Edward Schmidt, and Vernon Towle. *A Model for Intracortical Visual Prosthesis Research*. Artificial Organs. 27(11):1005-1015, 2003.

Jonathan Coulombe, Sylvain Carniguian, and Mohamad Sawan, *A Power Efficient Electronic Implant for a Visual Cortical Neuroprosthesis*, Artificial Organs. 29(3):233-238. 2005.

Rajiv Saigal, Costantino Renzi, and Vivian K. Mushahwar, *Intraspinal Microstimulation Generates Functional Movements After Spinal-Cord Injury*, IEEE Transactions on Neural Systems and Rehabilitation Engineering, Vol. 12, No. 4, 2004.

Victor Pikov and Douglas B. McCreery, *Mapping of Spinal Cord Circuits Controlling the Bladder and External Urethral Sphincter Functions in the Rabbit*. Neurourology and Urodynamics 23:172-179 (2004).

Douglas McCreery, Victor Pikov, Albert Lossinsky, Leo Bullara, and William Agnew, *Arrays for Chronic Functional Microstimulation of the Lumbosacral Spinal Cord*. IEEE Transactions on neural systems and Rehabilitation, Vol. 12, No. 2, 2004.

Changfeng Tai, August M. Booth, Charles J. Robinson, William C. de Groat, and James R. Roppolo, *Isometric Torque About the Knee Joint Generated by Microstimulation of the Cat L6 Spinal Cord*. IEEE Transactions on neural systems and Rehabilitation, Vol. 7, No. 1, 1999.

Lisa Guevremont, Costantino G. Renzi, Jonathan A. Norton, Jan Kowalczewski, Rajiv Saigal, and Vivian K. Mushahwar, *Locomotor-Related Networks in the Lumbosacral Enlargement of the Adult Spinal Cat: Activation Through Intraspinal Microstimulation*. IEEE Transactions on neural systems and Rehabilitation, Vol. 14, No. 3, 2006.

Changfeng Tai, August M. Booth, Charles J. Robinson, William C. de Groat, and James R. Roppoloa, *Multi-joint movement of the cat hindlimb evoked by microstimulation of the lumbosacral spinal cord*. Experimental Neurology 183 (2003) 620-627.

M. M. Pinter, F. Gerstenbrand, and M. R. Dimitrijevic, *Epidural electrical stimulation of posterior structures of the human lumbosacral cord: 3. Control of Spasticity*. Spinal Cord (2000) 38, 524-531.

B. Jilge, K. Minassian, F. Rattay, M. M. Pinter, F. Gerstenbrand, H. Binder, M. R. Dimitrijevic. *Initiating extension of the lower limbs in subjects with complete spinal cord injury by epidural lumbar cord stimulation*. Exp Brain Res (2004) 154: 308-326

K. Minassian, B. Jilge, F. Rattay, M. M. Pinter, H. Binder, F. Gerstenbrand and M. R. Dimitrijevic, *Stepping-like movements in humans with complete spinal cord injury induced by epidural stimulation of the lumbar cord: electromyographic study of compound muscle action potentials*. Spinal Cord (2004) 42, 401-416.

However, these stimulation therapies may not be effective for persons suffering from complete spinal cord injuries, when no motor function or sensation remains below the injury site, or for restoring more complex motor functions and skills such as standing up and walking. Therefore, a need remains for a device that enhances or restores motor function for persons suffering from spinal cord injuries, including more severe injuries such as complete spinal cord injuries.

SUMMARY

A system for enhancing or restoring motor function for a person suffering from spinal cord injury may detect nerve signals and stimulate nerves based on the detected signals. In particular, electrode devices may be implanted in the spinal cord that are in communication with each other and capable of detecting signals and/or stimulating the spinal cord. The electrode devices may interact with processors separate from the electrode devices that may process signals, generate stimulation signals, and offer a user interface with which to modify processor or electrode device settings.

In one aspect of the invention, a system for transferring spinal cord signals includes a superior electrode for interfacing with a first portion of a spinal cord of a human body and an inferior electrode for interfacing with a second portion of the spinal cord. The superior electrode has at least one superior contact for receiving signals from the first portion of the spinal cord to transmit to the inferior electrode. The inferior electrode has at least one inferior contact for transmitting signals received from the superior electrode to the second portion of the spinal cord.

In one embodiment, the inferior electrode has at least one inferior contact for receiving signals from the second portion of the spinal cord to transmit to the superior electrode; and the superior electrode has at least one superior contact for transmitting signals received from the inferior electrode to the first portion of the spinal cord. Any superior contacts or inferior contacts may be individually addressable.

In another embodiment, the superior electrode penetrates the first portion of the spinal cord and the inferior electrode penetrates the second portion of the spinal cord. The first portion of the spinal cord is within a superior segment of the spinal cord that is anatomically intact and in contact with the brain of the human body. The second portion of the spinal cord is within an inferior segment of the spinal cord that is anatomically intact and separate from the superior segment.

In another embodiment, the system includes a plurality of superior electrodes for interfacing with the first portion of the spinal cord and a plurality of inferior electrodes for interfacing with the second portion of the spinal cord.

In another embodiment, the system includes a superior backing coupled to the plurality of superior electrodes to form an array and an inferior backing coupled to the plurality of inferior electrodes in an array. The superior backing and the inferior backing may be curved to match a curvature of the spinal cord, implanted within a subdural space of the spinal cord, and/or composed of bio-compatible materials. The superior and/or inferior backing may measure between about 0.5 cm and about 3 cm along either an axis substantially parallel to the spinal cord or an axis substantially perpendicular to the spinal cord.

In another embodiment, the superior electrode and the inferior electrode are along a first lateral side of the spinal cord. A second superior electrode and a second inferior electrode may be along a second lateral side of the spinal cord.

In another embodiment, the superior electrode and the inferior electrode are along a dorsal side of the spinal cord.

In another embodiment, the system includes processing circuitry for processing signals transferred between the superior electrode and the inferior electrode. The processing circuitry may includes an amplifier for amplifying received signals, a power supply for generating power for the processing circuitry, a stimulator for sending stimulation signals, a switching matrix for selectively coupling an electrode to the stimulator, a processor for modifying signals, a programming interface for modifying the processor and for interfacing with a programming device external to the human body, a wireless transmitter for wirelessly transmitting the signals received from a portion of the spinal cord, and a wireless receiver for wirelessly receiving signals transmitted by the wireless transmitter. The power supply may be external to a dura of the spinal cord; and the processing circuitry may be implanted within a subdural space of the spinal cord.

In another embodiment, the system includes a superior wire coupled to the superior electrode and an inferior wire coupled to the inferior electrode. The superior wire and the inferior wire may be implanted within a subdural space of the spinal cord.

BRIEF DESCRIPTION

In the detailed description which follows, reference will be made to the attached drawings, in which.

DETAILED DESCRIPTION

Systems and methods for transferring signals from one portion of the spinal cord to another are provided. Signals may be generated or detected via electrode assemblies implanted in the spinal cord. Detected signals may be processed via a processor implanted in the body or external to the body, allowing a user to modify the processing of the signals. Signals to be transmitted on the spinal cord may be generated based on the detected signals.

Figure 1:
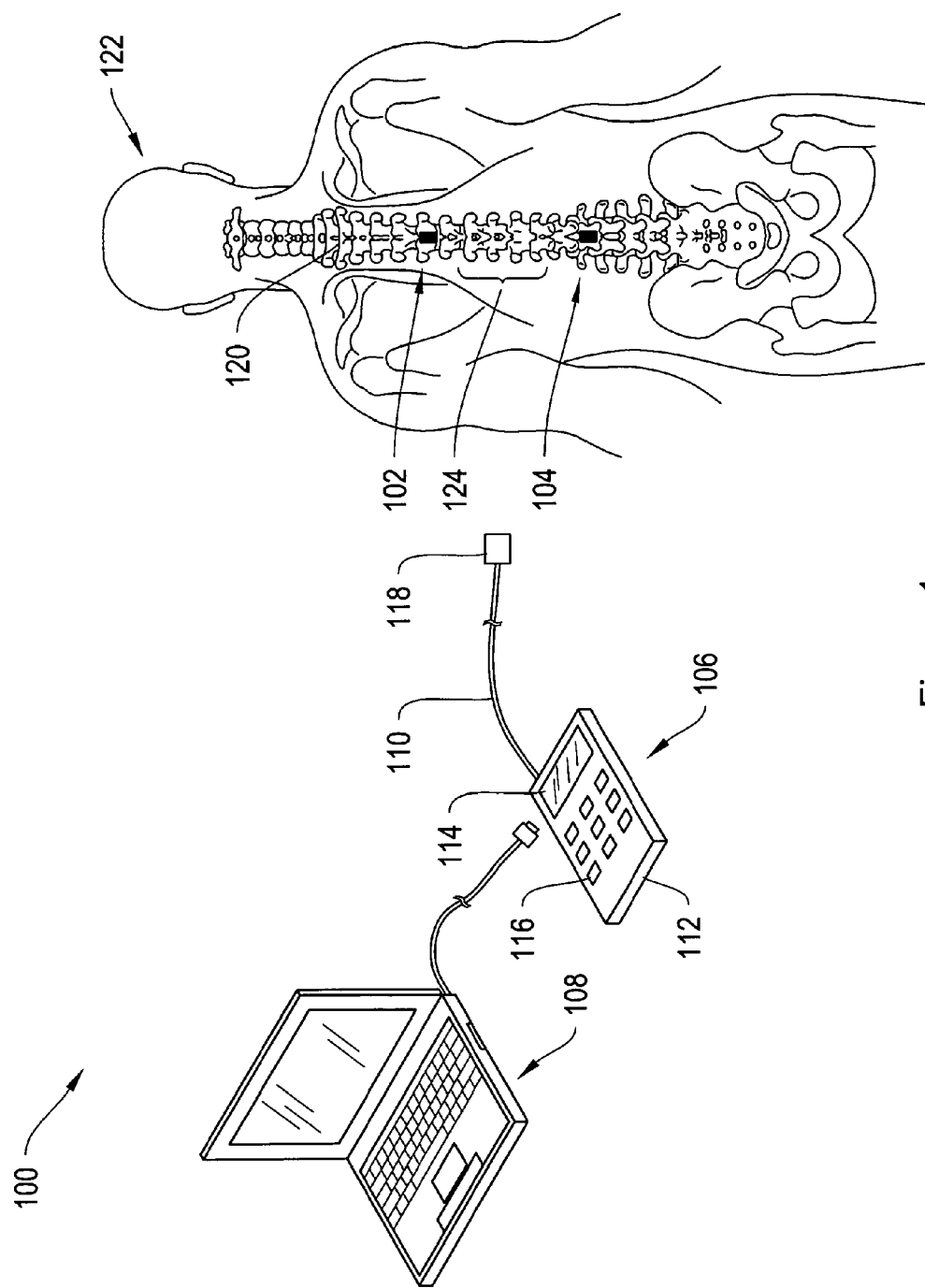
FIG. 1 depicts an exemplary spinal cord transfer interface system, according to one aspect of the invention.

FIG. 1 depicts an exemplary spinal cord transfer interface system 100 according to one embodiment of the invention. The spinal cord transfer interface system 100 includes a superior electrode assembly 102 and an inferior electrode assembly 104 each implanted in the spinal cord 120 of a patient 122 having a spinal cord injury 124, a remote device 106 for interfacing with and modifying the electrode assemblies 102 and 104, and a computer 108 for interfacing with and modifying the remote device 106.

The superior electrode assembly 102 is implanted in a region of the spinal cord 120 superior to any site of injury 124 on the spinal cord 120, and is capable of receiving signals from the patient's brain. The signals are transmitted, potentially wirelessly, to the inferior electrode assembly 104 which is located inferior to a site of injury 124 on the spinal cord 120 and stimulates the spinal cord 120 based on the signals received from the superior electrode assembly 102. In addition, the inferior electrode assembly 104 can receive signals that originated from the peripheral nervous system and transmit, potentially wirelessly, the signals to the superior electrode assembly 102, which in turn can stimulate the spinal cord 120 to send signals to the brain. Processing circuitry located at the superior electrode assembly 102, located at the inferior electrode assembly 104, and/or elsewhere implanted in the body of the patient can process the signals received by the superior electrode assembly 102 and/or the inferior electrode assembly 104 to aid in generating signals with which to stimulate the spinal cord 120. The superior electrode assembly 102 and the inferior electrode assembly 104 are described further below.

The remote device 106 is capable of altering settings of the processing circuitry to modify how the processing circuitry processes received signals and generates signals for stimulation. The remote device 106 includes a processing interface 118 that when placed on the patient adjacent to the processing circuitry serves to wirelessly communicate the desired alterations to the processing circuitry. The processing interface 118 receives the desired alterations via a wire 110 attached to the housing 112 of the remote device 106. The housing 112 includes user interface features, such as a display 114 and buttons 116, that allow a user to select alterations. For example, certain buttons 116 may correspond to specific actions, such as standing or sitting up, that the patient would like to perform. Other buttons 116 may correspond to increasing or decreasing the intensity or strength of stimulating signals. Other user interface mechanisms such as dials, switches, or touch-screens may also be included in the remote device 106. The remote device 106 may be used by the patient or by someone else who is aiding the patient to perform or learn certain activities, possibly as part of a physical therapy regimen. In the case where processing circuitry is located at both the superior electrode assembly 102 and the inferior electrode assembly 104, the remote device 106 may be connected via wire to a second processing interface (not depicted) similar to the processing interface 118 depicted. The processing interface 118 may be placed adjacent to one of the electrode assemblies while the second processing interface is placed adjacent to the other electrode assembly to simultaneously communicate with processing circuitry at both locations.

The remote device 106 may have a port with which to connect to a computer 108. The computer 108 may reprogram the buttons 116 of the remote device 106 to correspond to different actions or to improve the efficacy of the settings corresponding to certain actions. In one embodiment, the processing interface 118 may receive signals from the processing circuitry that originated either from the brain or the peripheral nervous system, which are then transmitted to the remote device, which in turn transmits the received signals to the computer 108 for storage, inspection, and/or to assist in determining how best to process the received signals to generate stimulation signals. Different options for processing the received signals may be stored on the remote device and assigned to different buttons 116. Stimulation signals may be generated by the computer and transmitted via the remote device 106 to the processing interface 118, which transmits the stimulation signals to the appropriate electrode assembly to stimulate the spinal cord.

Figure 2A:
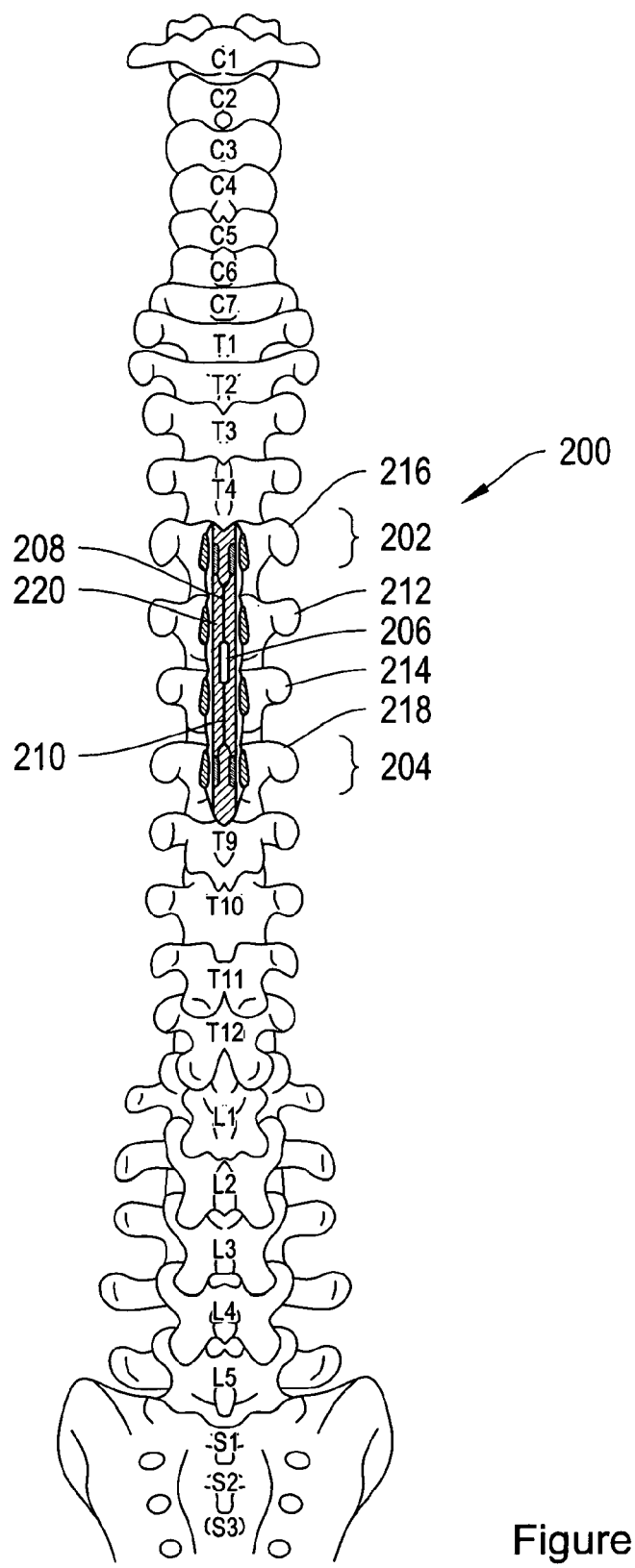
FIGS. 2A and 2B depict dorsal views of an exemplary spinal cord implant, according to one aspect of the invention.
Figure 2B:
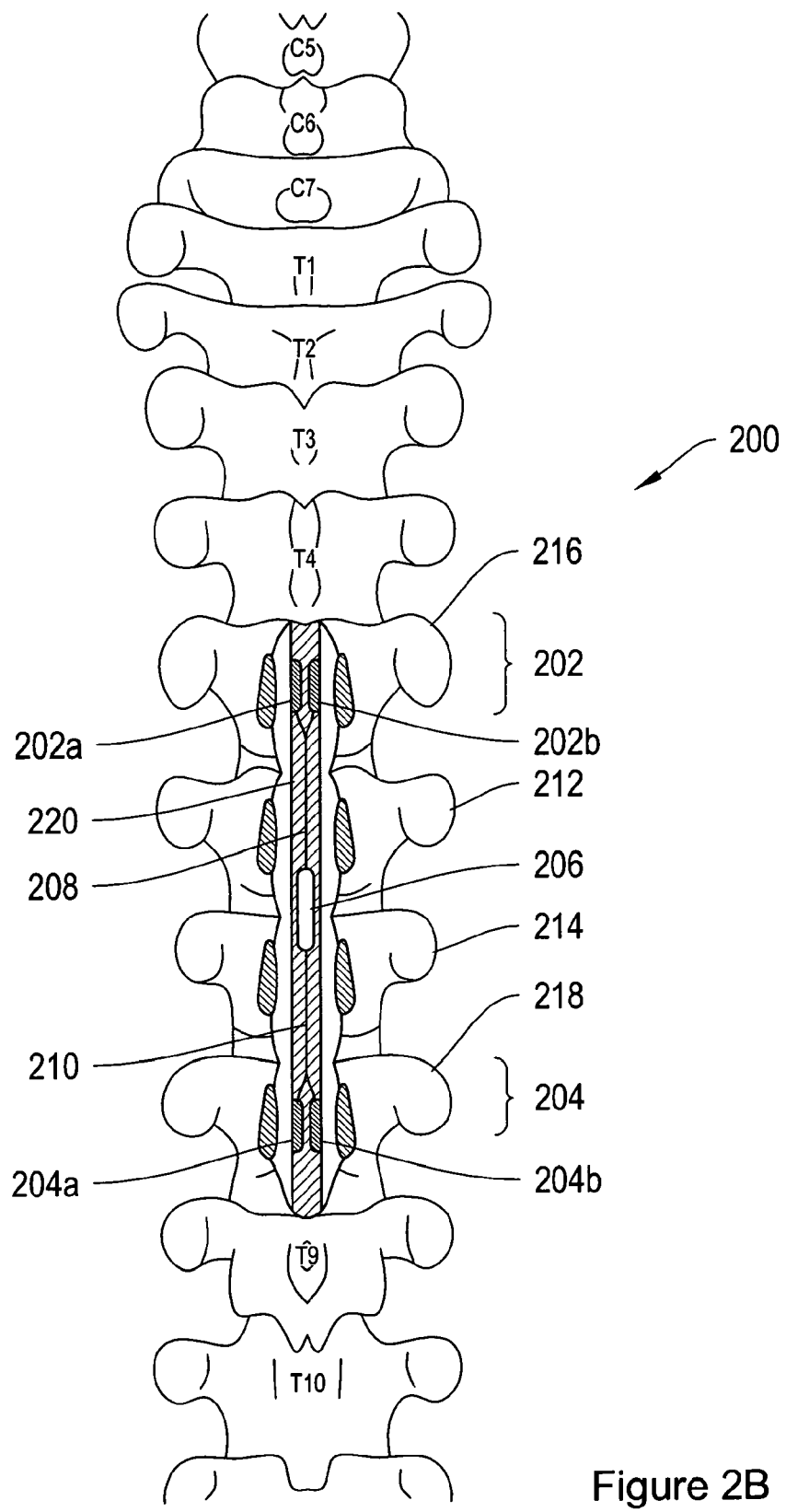

FIGS. 2A and 2B depict dorsal views of an exemplary spinal cord implant 200 having a superior electrode assembly 202, an inferior electrode assembly 204, and processing circuitry 206, and implanted in a patient having a spinal cord injury approximately near the T6 vertebra 212 or the T7 vertebra 214. The superior electrode assembly 202 and the inferior electrode assembly 204 are disposed approximately near the T5 vertebra 216 and the T8 vertebra 218, respectively. Other injury sites along the spinal cord 220 may also benefit from a spinal cord implant system as described herein, where the superior electrode assembly is typically implanted superior to any injury site while the inferior electrode assembly is typically implanted inferior to any injury site.

The superior electrode assembly 202 and the inferior electrode assembly 204 each have at least one electrode array, in this case superior electrode arrays 202a and 202b and inferior electrode arrays 204a and 204b. Each electrode array has an electrode backing attached to a plurality of electrodes that pierce the spinal cord 220 to receive and/or transmit signals, which are described further below. The superior electrode arrays 202a and 202b are attached to and communicate signals via a superior wire 208 that is connected to the processing circuitry 206. Similarly, the inferior electrode arrays 204a and 204b are attached to and communicate signals via an inferior wire 210 that is also connected to the processing circuitry 206. The electrode arrays 202a, 202b, 204a, and 204b, processing circuitry 206, and wires 208 and 210 are all implanted in a subdural space, which is accessed by first performing a laminectomy, a surgical procedure to access the spinal cord dorsally by removing the lamina of the vertebrae, and then slicing open the dura mater to expose the subdural space. After implanting the assemblies 202 and 204, the wires 208, and 210, and the processing circuitry 206, the dura mater may be sewn closed to prevent leakage of cerebrospinal fluid. In this embodiment, in which wires are used to communicate signals between superior and inferior electrode assemblies 202 and 204, it can be necessary to remove the lamina of all vertebrae between the superior and inferior electrode assemblies 202 and 204.

Figure 3:
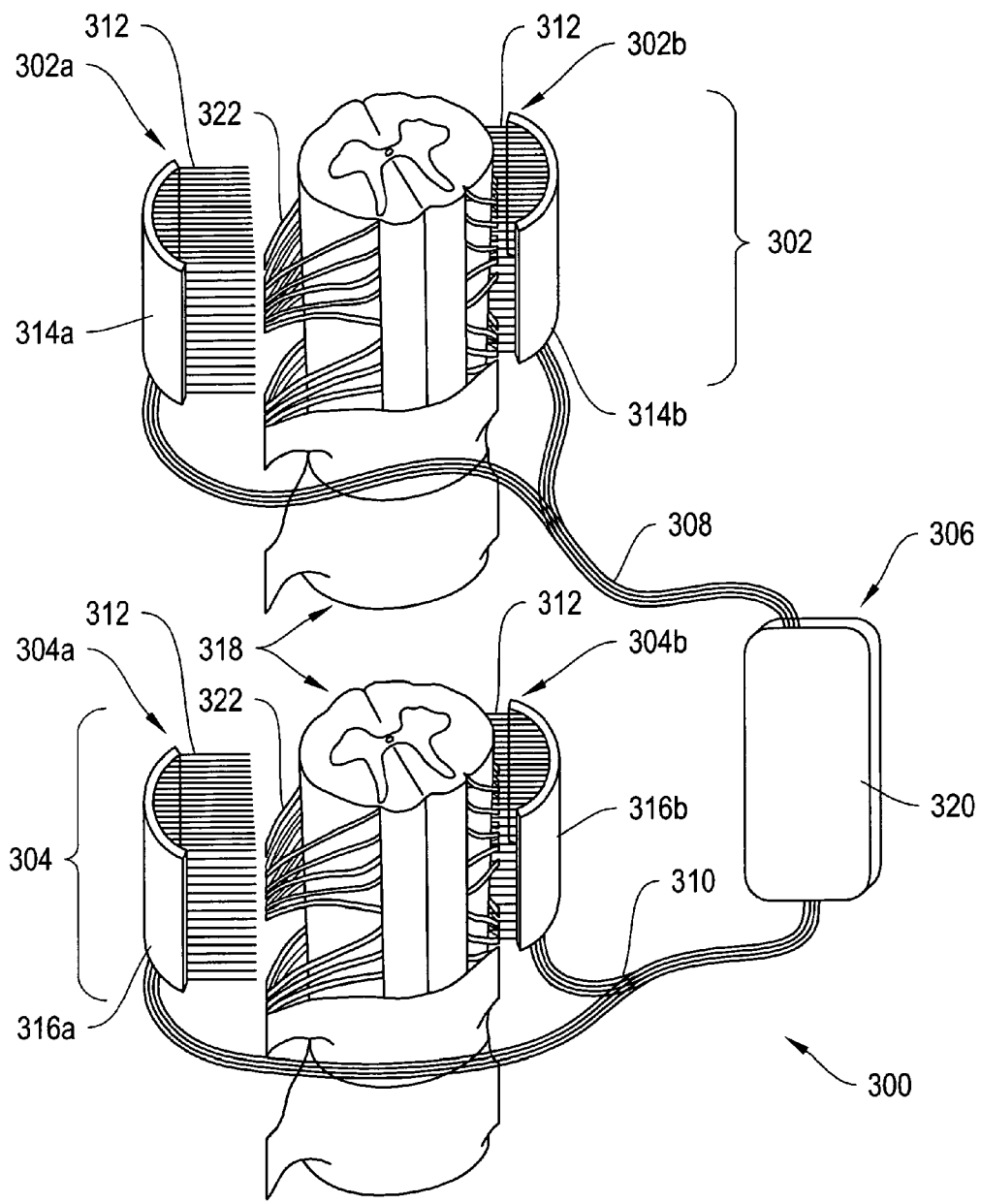
FIG. 3 depicts an exemplary spinal cord implant similar to the spinal cord implant of FIG. 2, according to one aspect of the invention.

FIG. 3 depicts an exemplary spinal cord implant 300 similar to the spinal cord implant 200 of FIG. 2, also having a superior electrode assembly 302 comprising two superior electrode arrays 302a and 302b, an inferior electrode assembly 304 comprising two inferior electrode arrays 304a and 304b, and processing circuitry 306 connected to the superior electrode assembly 302 and the inferior electrode assembly 304 via a superior wire 308 and an inferior wire 310, respectively. Each electrode array includes a plurality of electrodes 312 disposed substantially parallel to one another and attached to a backing, namely superior backings 314a and 314b and inferior backings 316a and 316b, which can be made of any substantially rigid biocompatible material such as platinum-iridium or surgical grade stainless steel with a suitable coating like Silastic. The electrodes 312 when implanted pierce through the spinal cord 318, with each electrode having a plurality of contacts. The superior electrode assembly 302 and the inferior electrode assembly 304 are each depicted relative to a section of spinal cord 318, and in particular their respective electrodes are shown as potentially piercing the spinal cord 318 laterally. In another embodiment, the electrodes pierce the spinal cord 318 laterally at sections of the spinal cord 318 free from nerves 322. The processing circuitry 306 has a housing 320 which can be made of platinum-iridium or surgical grade stainless steel with a suitable coating like Silastic, or any other biocompatible material.

Figure 4A:
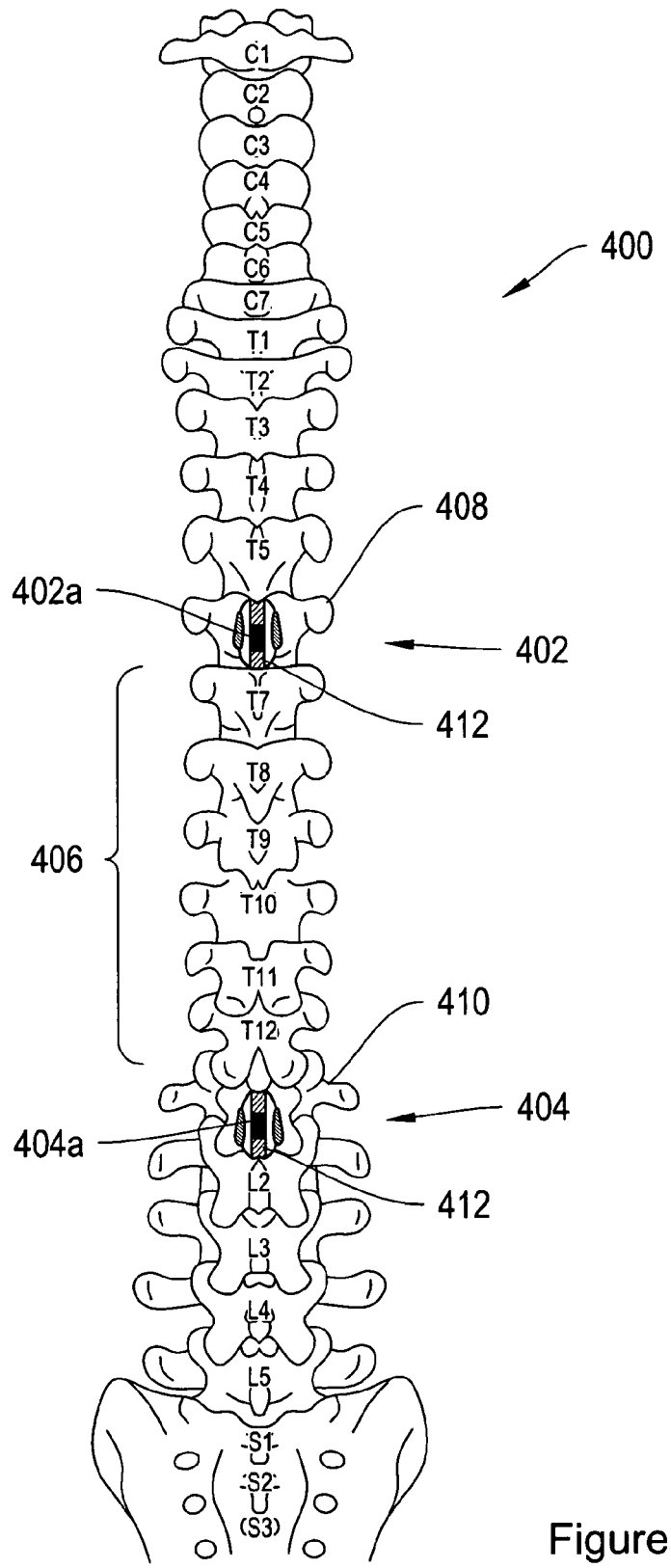
FIGS. 4A and 4B depict dorsal views of an exemplary spinal cord implant, according to one aspect of the invention.
Figure 4B:
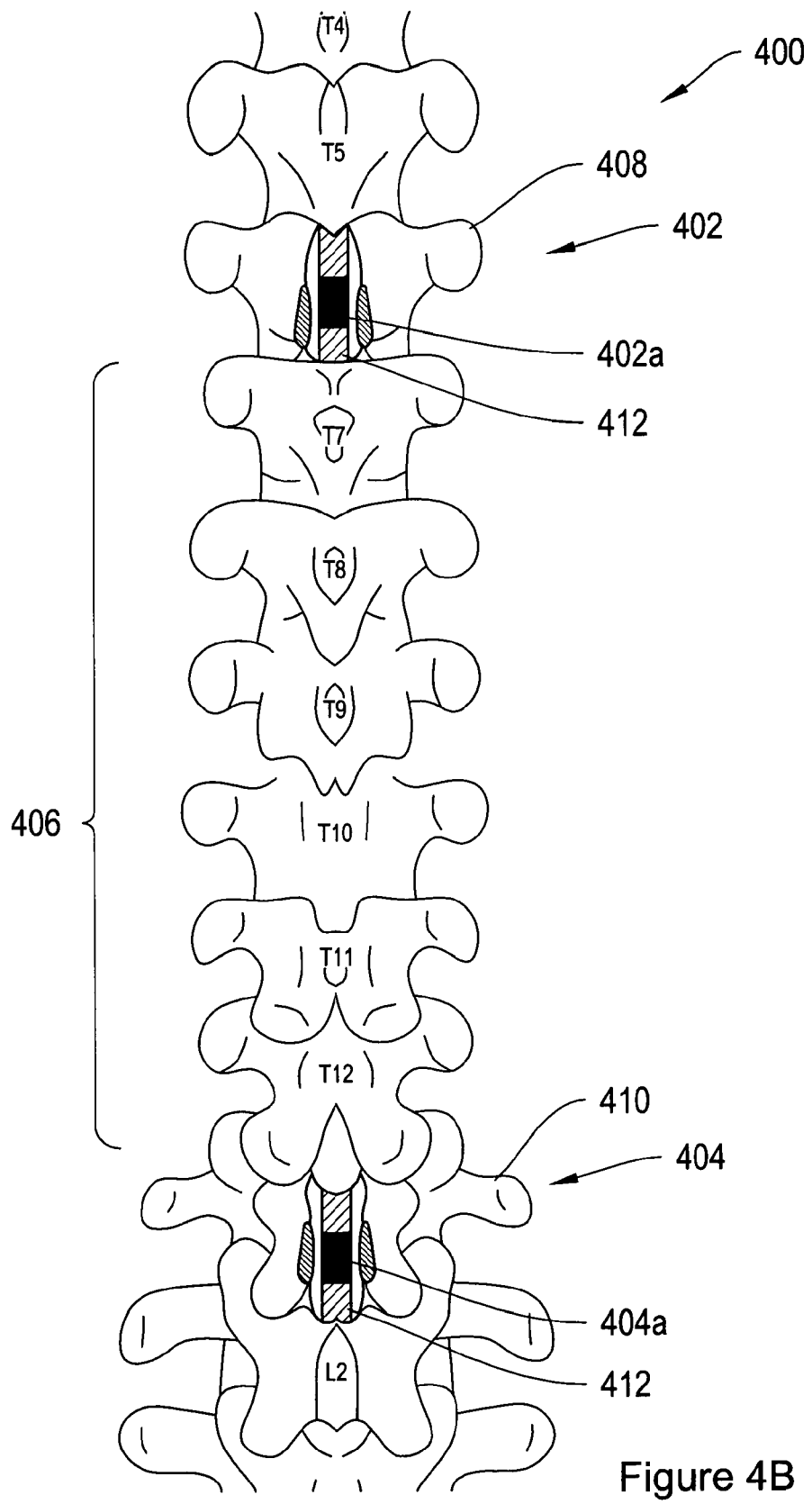

FIGS. 4A and 4B depict dorsal views of an exemplary spinal cord implant 400 having a superior electrode assembly 402 and an inferior electrode assembly 404 implanted in a patient having a spinal cord injury approximately near at least one of the T7 through T12 vertebrae 406. The superior electrode assembly 402 and the inferior electrode assembly 404 are disposed approximately near the T6 vertebra 408 and the L1 vertebra 410, respectively. Other injury sites along the spinal cord 412 may also benefit from a spinal cord implant system as described herein, where the superior electrode assembly is typically implanted superior to any injury site while the inferior electrode assembly is typically implanted inferior to any injury site.

The superior electrode assembly 402 and the inferior electrode assembly 404 each have an electrode array, in this case superior electrode array 402a and inferior electrode array 404a. Each electrode array has an electrode backing attached to a plurality of electrodes that pierce the spinal cord 412 to receive and/or transmit signals, which are described further below. The superior electrode assembly 402 and the inferior electrode assembly 404 communicate signals wirelessly and are each implanted in a subdural space, which is accessed by first performing a laminectomy, a surgical procedure to access the spinal cord 412 dorsally by removing the lamina of the vertebrae, and then slicing open the dura mater to expose the subdural space. After implanting the assemblies 402 and 404, the dura mater may be sewn closed to prevent leakage of cerebrospinal fluid. In this embodiment in which the signals are communicated wirelessly between the superior and inferior implantation sites, it can be necessary to remove the lamina of only the vertebrae at the implantation sites. For example, FIGS. 4A and 4B depict the T6 408 and L1 410 vertebrae after having had laminectomies performed, while the intervening vertebrae 406 remain intact.

Figure 5:
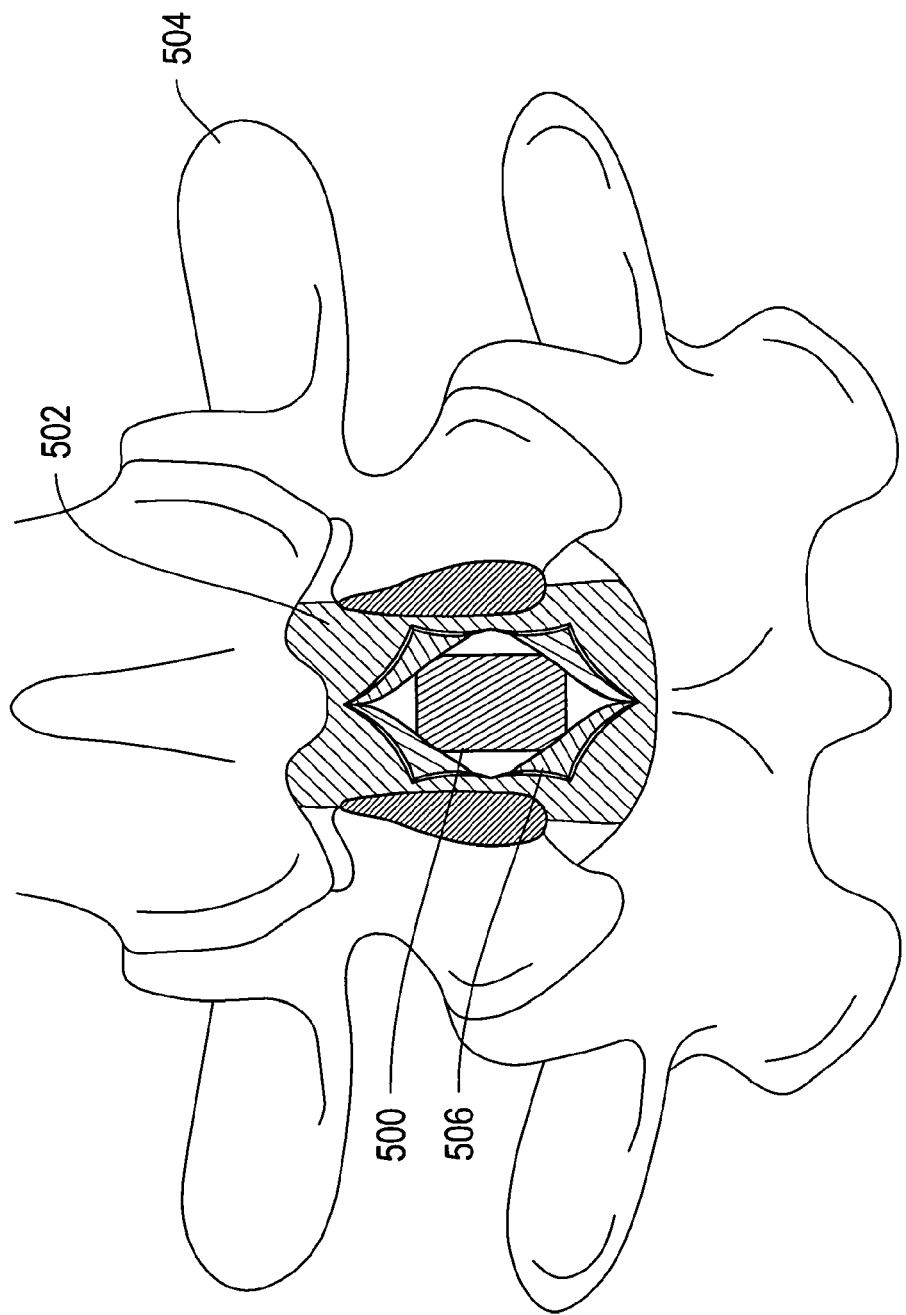
FIG. 5 depicts a dorsal view of an exemplary electrode assembly implanted dorsally in a subdural space of a spinal cord, similar to electrode assemblies depicted in FIGS. 4A and 4B, according to one aspect of the invention.

FIG. 5 depicts a dorsal view of an exemplary electrode assembly 500 implanted dorsally in a subdural space of a spinal cord 502, similar to either superior electrode assembly 402 or inferior electrode assembly 404 both depicted in FIGS. 4A and 4B. The electrode assembly 500 can include a wireless receiver and/or transmitter and processing circuitry that can be reprogrammed using a processing interface similar to processing interface 118 of FIG. 1. To access the section of the spinal cord 502 in which the electrode assembly 500 is implanted, a laminectomy, which removes the lamina, has been performed to the vertebra 504 immediately adjacent to the relevant section of the spinal cord 502. The removal of the lamina facilitates transcutaneous communication between the processing circuitry and the processing interface 118, which in use is placed externally on the surface of the skin. In addition, the dura mater 506 has been cut open and pulled back to expose the subdural space in which the electrode assembly 500 is implanted.

Figure 6:
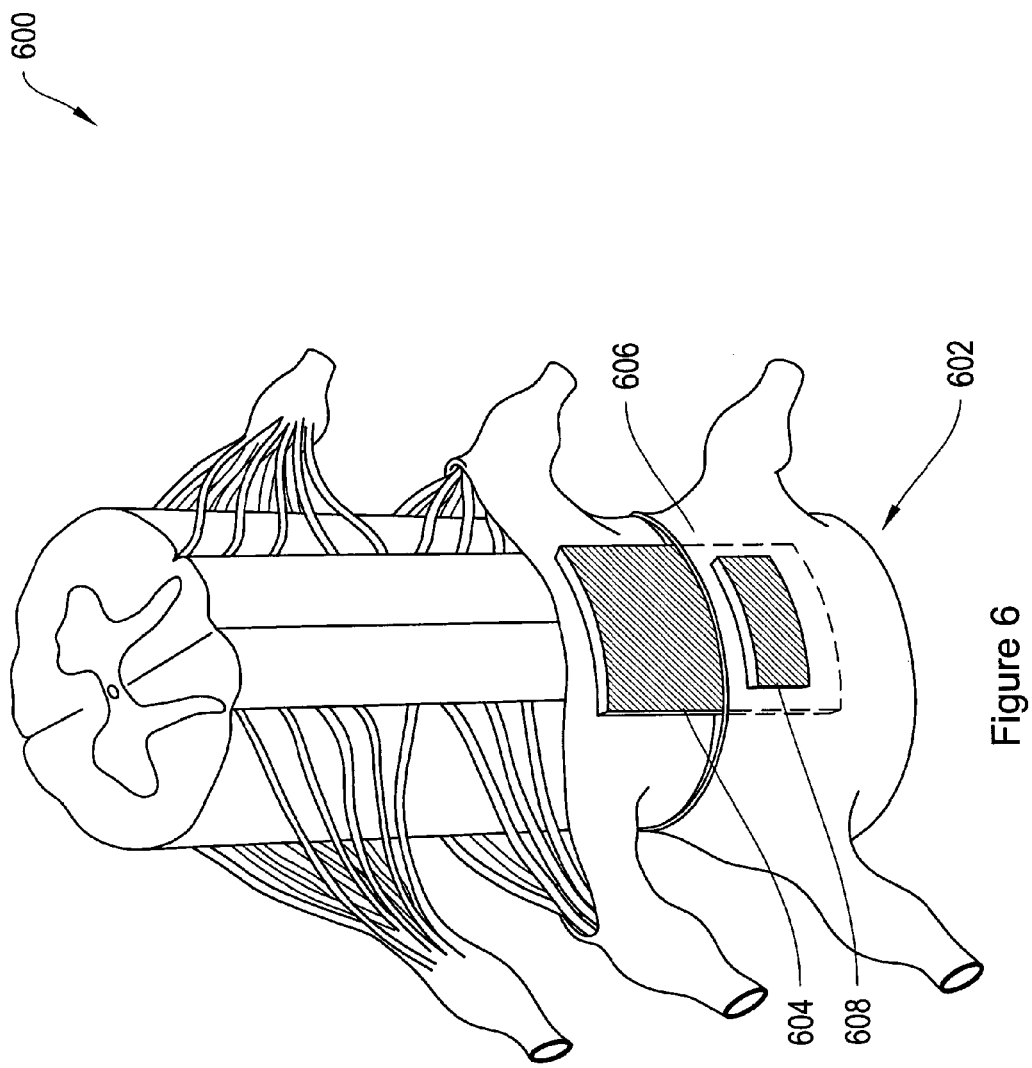
FIG. 6 depicts an oblique dorsal view of an exemplary electrode assembly implanted dorsally in a section of spinal cord, according to one aspect of the invention.

FIG. 6 depicts an oblique dorsal view of an exemplary electrode assembly 600 implanted dorsally in a section of spinal cord 602 of a patient, which can be either a superior electrode assembly or an inferior electrode assembly. The electrode assembly 600 includes an electrode backing 604 disposed under the dura mater 606, a power supply 608 disposed outside the dura mater 606, and processing circuitry contained within the housing for the electrode backing 604 and/or within the housing for the power supply 608. The electrode backing 604 is attached to a plurality of electrodes (not depicted) that pierce the spinal cord 602 to receive signals from and/or transmit signals to the spinal cord 602. The signals are generated and/or processed by the processing circuitry, which is powered by the power supply 608. As the power supply 608 may need replacement more often than the other parts of the electrode assembly 600, the power supply 608 is implanted externally to the dura mater 606. Implants outside the dura mater 606 are typically easier to access than any subdural implant which over time may develop scarring that further inhibits removal of the subdural implant. In one embodiment, the housing of the power supply 608 includes flanges which may be sewn to the dura mater 606 to secure the power supply 608 substantially near the rest of the electrode assembly 600. The processing circuitry can include wireless receivers and/or transmitters to communicate with another electrode assembly and/or a processing interface placed adjacent to the electrode assembly 600 and external to the skin of the patient.

Figure 7:
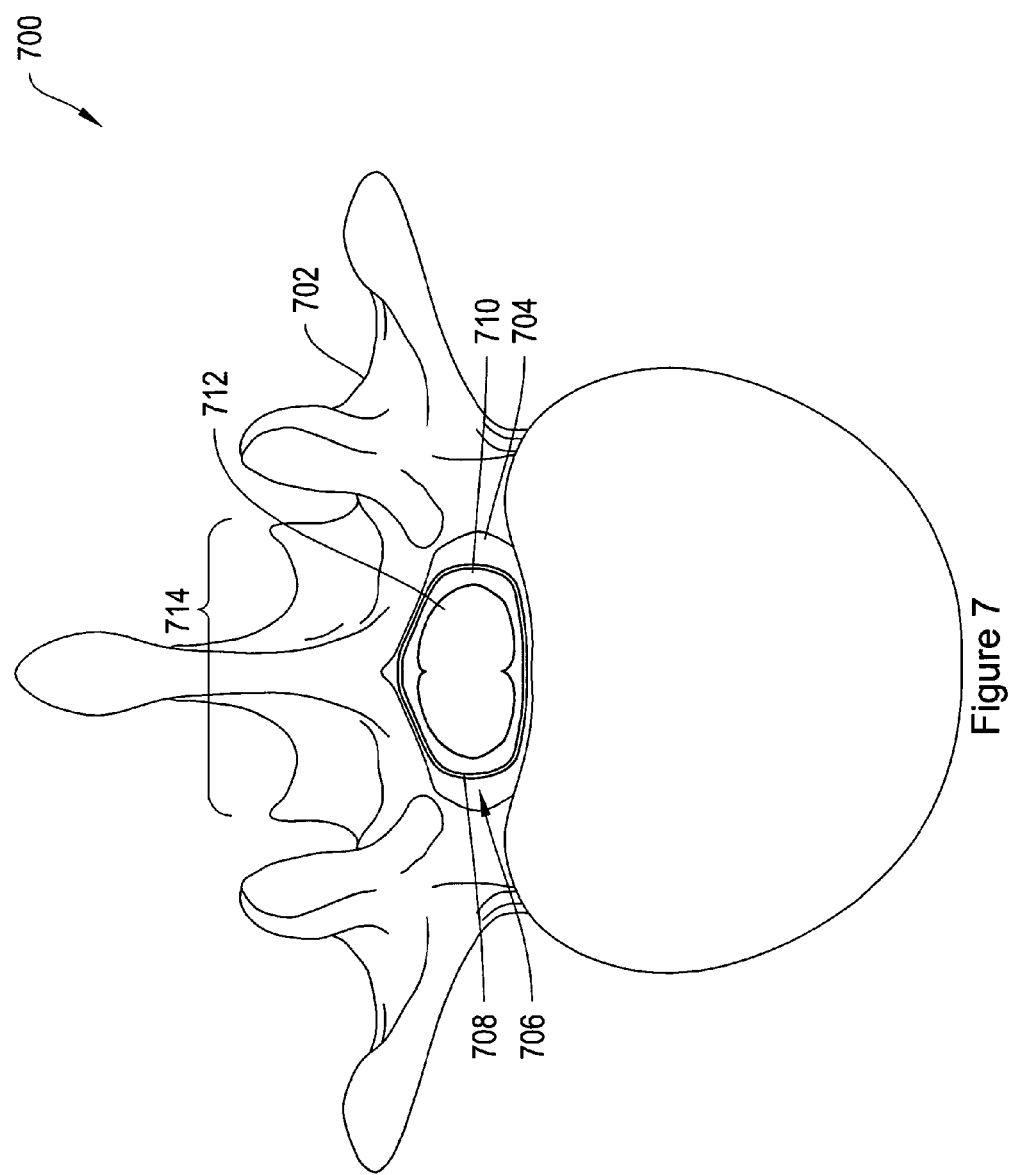
FIG. 7 depicts a cross-sectional view of an exemplary spinal column of a patient in which a spinal cord implant may be disposed.

FIG. 7 depicts a cross-sectional view of an exemplary spinal column 700 of a patient in which a spinal cord implant may be disposed according to one aspect of this invention. The spinal column 700 comprises a vertebra 702 through which runs a spinal canal 704 in which resides a spinal cord 706. The spinal cord 706 has a dura mater 708, namely a tough outer layer that surrounds the rest of the spinal cord 712 and is separated from the rest of the spinal cord 712 by a subdural space 710 containing cerebrospinal fluid. The rest of the spinal cord 712 includes the nerves of the central nervous system. The vertebra 702 includes a section of bone posterior to the spinal cord 706 known as the lamina 714 of the vertebra 702. A procedure well-known in the art, known as a laminectomy, can remove the lamina 714.

Figure 8:
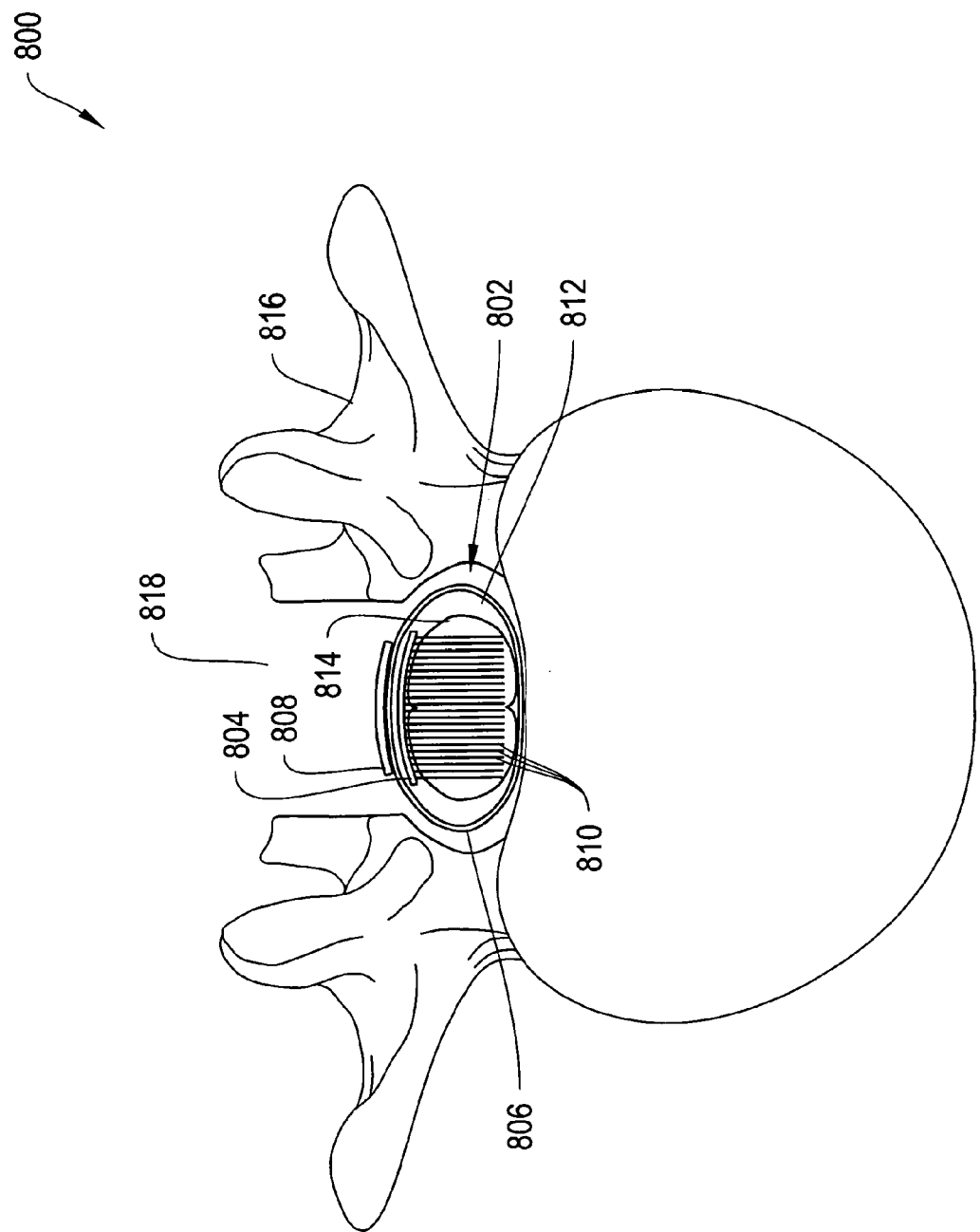
FIG. 8 depicts a cross-sectional view of an exemplary electrode assembly implanted dorsally in a spinal cord, similar to the electrode assembly depicted in FIG. 6, according to one aspect of the invention.

FIG. 8 depicts a cross-sectional view of an exemplary electrode assembly 800 implanted dorsally in a spinal cord 802 of a patient, similar to the electrode assembly 600 depicted in FIG. 6 and which can be either a superior electrode assembly or an inferior electrode assembly. The electrode assembly 800 includes an electrode backing 804 disposed within the dura mater 806 of the spinal cord 802 and in a subdural space 812, a power supply 808 disposed outside the dura mater 806, and processing circuitry contained within the housing for the electrode backing 804 and/or within the housing for the power supply 808. The electrode backing 804 is attached to a plurality of electrodes 810 disposed substantially parallel to one another and that pierce the inner spinal cord 814 to receive signals from and/or transmit signals to nerves contained within the inner spinal cord 814. The signals are generated and/or processed by the processing circuitry, which is powered by the power supply 808. As the power supply 808 may need replacement more often than the other parts of the electrode assembly 800, the power supply 808 is implanted externally to the dura mater 806. Implants outside the dura mater 806 are typically easier to access than any subdural implant which over time may develop scarring that further inhibits removal of the subdural implant. In one embodiment, the housing of the power supply 808 includes flanges which may be sewn to the dura mater 806 to secure the power supply 808 substantially near the rest of the electrode assembly 800. The processing circuitry can include wireless receivers and/or transmitters to communicate with another electrode assembly and/or a processing interface placed adjacent to the electrode assembly 800 and external to the skin of the patient. The vertebra 816 surrounding the section of spinal cord 802 depicted in FIG. 8 has had its lamina removed to allow access to the spinal cord 802, as shown by the empty space 818 located posterior to the electrode assembly 800.

Figure 9:
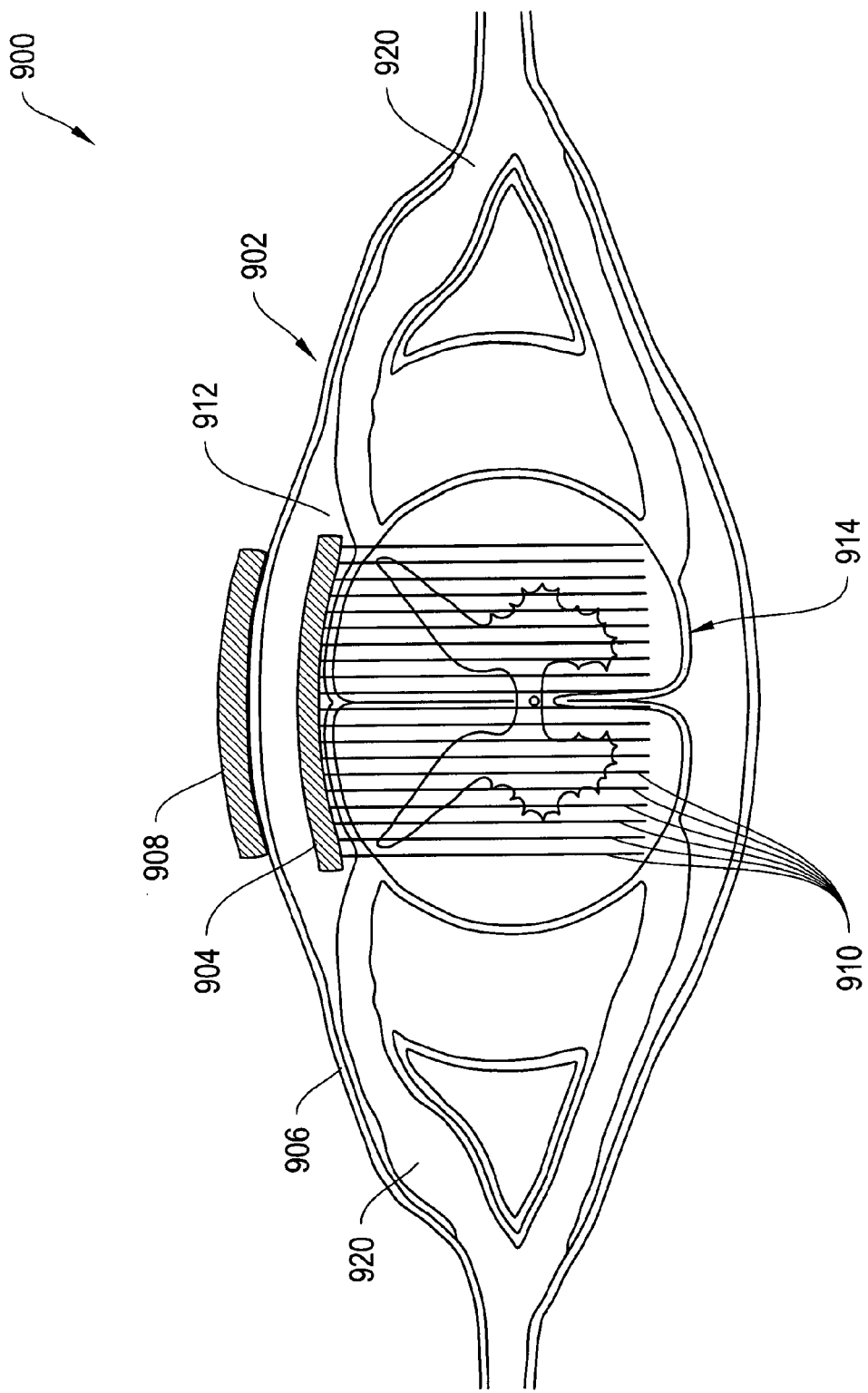
FIG. 9 depicts a cross-sectional view of an exemplary electrode assembly implanted dorsally in a section of a spinal cord, according to one aspect of the invention.

FIG. 9 depicts a cross-sectional view of an exemplary electrode assembly 900 implanted dorsally in a section of a spinal cord 902 of a patient to which nerves 920 are connected. The electrode assembly 900 is similar to the electrode assembly 600 depicted in FIG. 6 and can be either a superior electrode assembly or an inferior electrode assembly. The electrode assembly 900 includes an electrode backing 904 disposed within the dura mater 906 of the spinal cord 902 and in a subdural space 912 of the spinal cord 902, a power supply 908 disposed outside the dura mater 906, and processing circuitry contained within the housing for the electrode backing 904 and/or within the housing for the power supply 908. The electrode backing 904 is attached to a plurality of electrodes 910 disposed substantially parallel to one another and that pierce the inner spinal cord 914 to receive signals from and/or transmit signals to nerves contained within the inner spinal cord 914. In particular, each electrode has a plurality of contacts along a substantial portion of its length, where each contact is individually addressable, which allows each contact to receive or transmit a signal independently of all other contacts. The width of the electrode backing 904 and the lengths of the electrodes 910 are selected such that the electrodes are in contact with as many sections of the inner spinal cord 914 as possible so that signals may be received from or transmitted to as many sections of the spinal cord as possible. The signals are generated and/or processed by the processing circuitry, which is powered by the power supply 908. As the power supply 908 may need replacement more often than the other parts of the electrode assembly 900, the power supply 908 is implanted externally to the dura mater 906. Implants outside the dura mater 906 are typically easier to access than any subdural implant which over time may develop scarring that further inhibits removal of the subdural implant. In one embodiment, the housing of the power supply 908 includes flanges which may be sewn to the dura mater 906 to secure the power supply 908 substantially near the rest of the electrode assembly 900. The processing circuitry can include wireless receivers and/or transmitters to communicate with another electrode assembly and/or a processing interface placed adjacent to the electrode assembly 900 and external to the skin of the patient.

Figure 10:
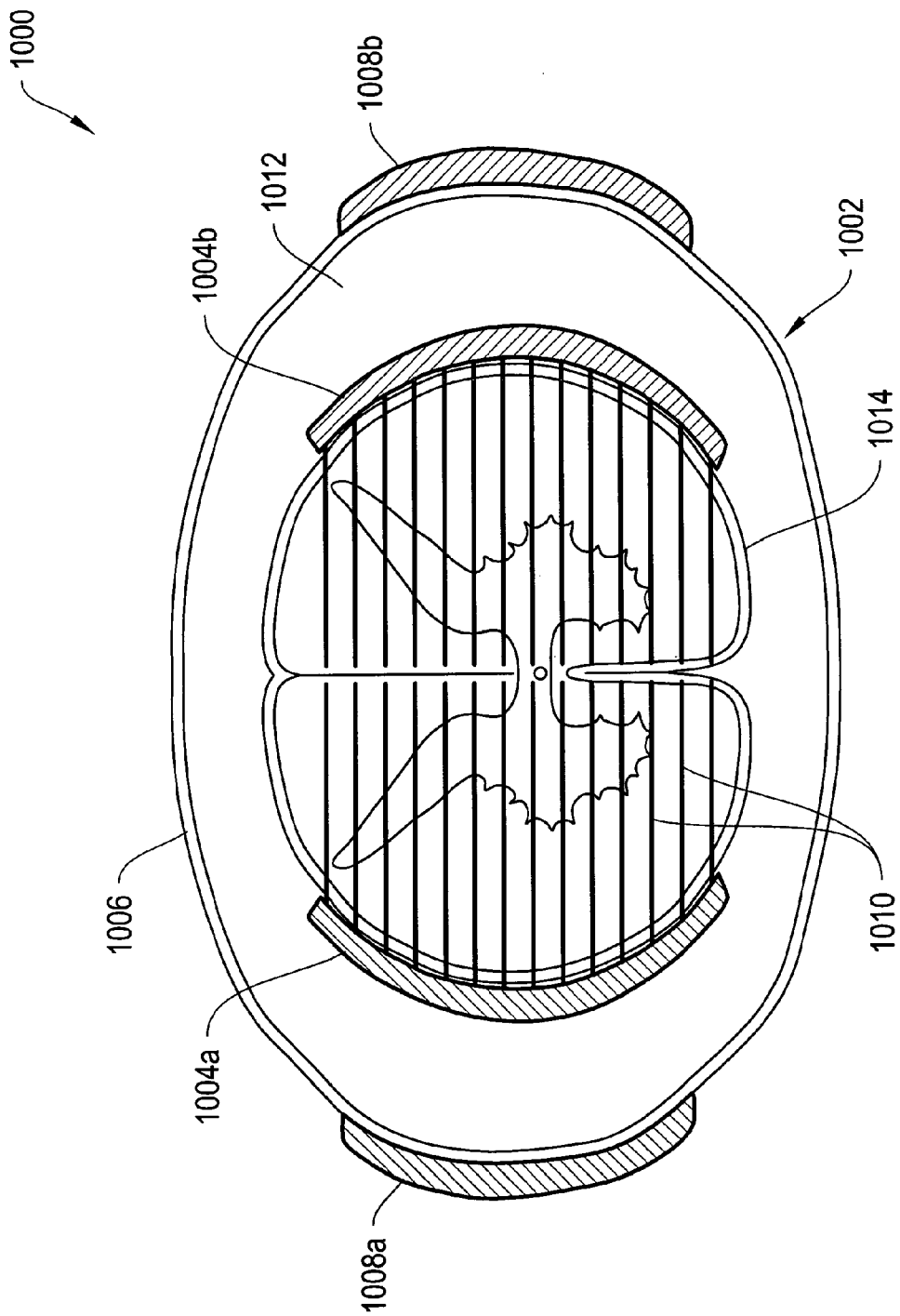
FIG. 10 depicts a cross-sectional view of an exemplary electrode assembly implanted laterally in a section of a spinal cord, similar to electrode assemblies depicted in FIG. 3, according to one aspect of the invention.

FIG. 10 depicts a cross-sectional view of an exemplary electrode assembly 1000 implanted laterally in a section of a spinal cord 1002 of a patient, similar to either the superior electrode assembly 302 or the inferior electrode assembly 304 depicted in FIG. 3. The electrode assembly 1000 includes electrode backings 1004a and 1004b disposed within the dura mater 1006 of the spinal cord 1002 and in a subdural space 1012 of the spinal cord 1002, power supplies 1008a and 1008b disposed outside the dura mater 1006, and processing circuitry contained within the housings for the electrode backings 1004a and 1004b and/or within the housings for the power supplies 1008a and 1008b. The electrode backings 1004a and 1004b are each attached to a plurality of electrodes 1010 disposed substantially parallel to one another and that pierce the inner spinal cord 1014 to receive signals from and/or transmit signals to nerves contained within the inner spinal cord 1014. In particular, each electrode has a plurality of contacts along a substantial portion of its length, where each contact is individually addressable, which allows each contact to receive or transmit a signal independently of all other contacts. The widths of the electrode backings 1004a and 1004b and the lengths of the electrodes 1010 are selected such that the electrodes are in contact with as many sections of the inner spinal cord 1014 as possible so that signals may be received from or transmitted to as many sections of the spinal cord as possible. The signals are generated and/or processed by the processing circuitry, which is powered by the power supply, 1008a or 1008b, closest to its corresponding electrode backing, 1004a or 1004b, respectively. As the power supplies 1008a and 1008b may need replacement more often than the other parts of the electrode assembly 1000, the power supplies 1008a and 1008b are implanted externally to the dura mater 1006. Implants outside the dura mater 1006 are typically easier to access than any subdural implant which over time may develop scarring that further inhibits removal of the subdural implant. In one embodiment, the housings of the power supplies 1008a and 1008b includes flanges which may be sewn to the dura mater 1006 to secure the power supplies 1008a and 1008b substantially near the rest of the electrode assembly 1000. The processing circuitry can include wireless receivers and/or transmitters to communicate with another electrode assembly and/or a processing interface placed adjacent to the electrode assembly 1000 and external to the skin of the patient.

Figure 11:
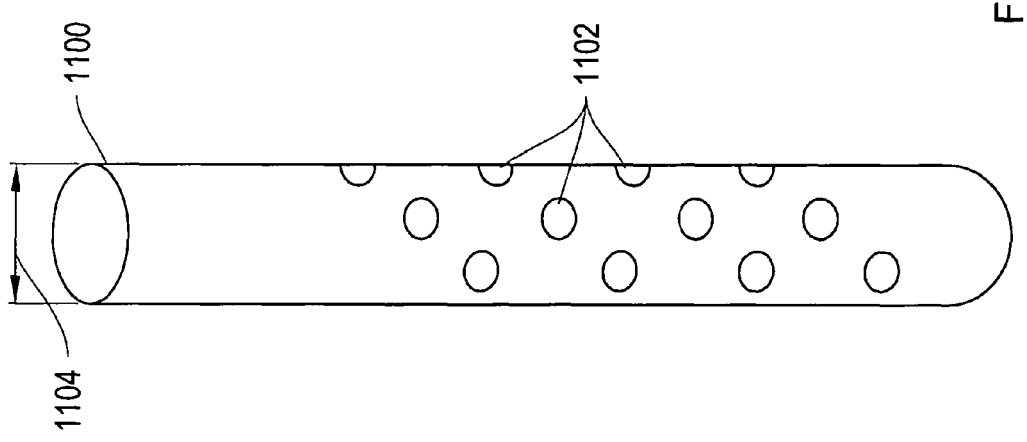
FIG. 11 depicts a portion of an exemplary electrode that may be used in the electrode assemblies described herein, according to one aspect of the invention.

FIG. 11 depicts a portion of an exemplary electrode 1100, similar to the electrodes 810, 910, and 1010 depicted in FIGS. 8, 9, and 10, respectively, that may be used in the electrode assemblies described above. The electrode 1100 has a plurality of contacts 1102 dispersed over its surface, where each contact 1102 may be individually addressable. The contacts 1102 may be made of platinum-iridium, or any other conductive, biocompatible, corrosion-resistant material. Electrode 1100 may be made via a deposition method and may range from about 100 to 200 microns in diameter 1104.

Figure 14:
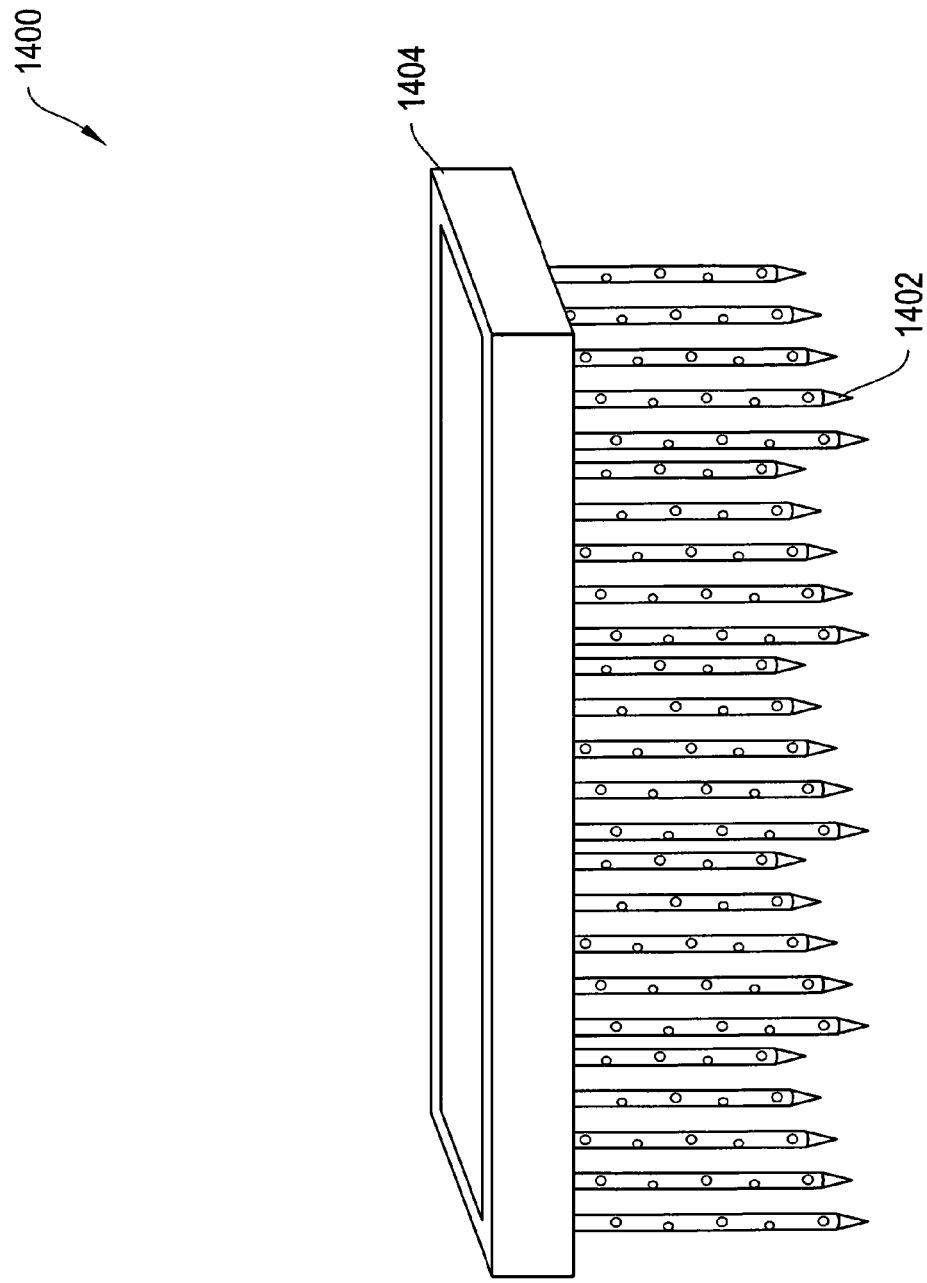
FIG. 14 depicts an exemplary electrode assembly employing electrodes similar to that depicted in FIG. 11, according to one aspect of the invention.
Figure 15:
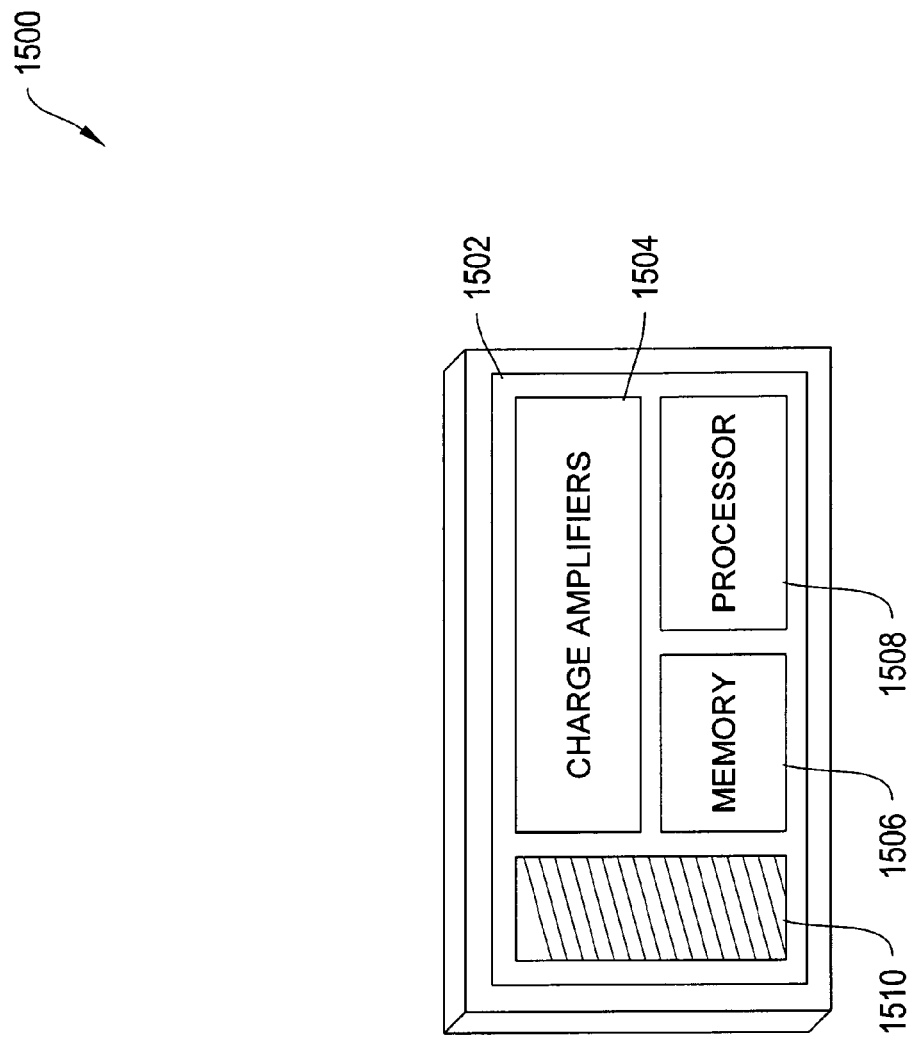
FIG. 15 depicts an exemplary substrate portion of an electrode assembly, according to one aspect of the invention.

FIG. 14 depicts an exemplary electrode assembly 1400, similar to the electrode assemblies described above, that employs a plurality of electrodes 1402 similar to electrode 1100, according to some aspects of the invention. The electrodes 1402 may have approximately a uniform length or may range in length. In some embodiments, the electrodes 1402 each have a length corresponding to a region of the spinal cord. For example, electrodes in contact with the conus region, when implanted, may have a length between about 1.5 cm and about 2 cm, while electrodes in contact with the thoracic region, when implanted, may have a length around 1 cm. Electrodes 1402 are attached to a substrate 1404 and may be spaced up to 500 microns apart from one another. In some embodiments, the substrate 1404 may have a depth ranging between about 1 mm and about 3 mm. The edges of the substrate 1404 may be rounded. Substrate 1404 may include processing circuitry for receiving and/or transmitting signals from the electrodes 1402 and communicating with devices external to the body in which electrode assembly 1400 is implanted, such as the devices described above with respect to FIG. 1. FIG. 15 depicts an exemplary substrate 1500, similar to the substrate 1404 of FIG. 14, having processing circuitry 1502 formed thereon, according to some aspects of the invention. The processing circuitry 1502 may include charge amplifiers 1504, memory 1506, and a processor 1508, and may be in communication with a coil 1510 for receiving and/or transmitting signals, such as radio frequency signals.

Figure 12:
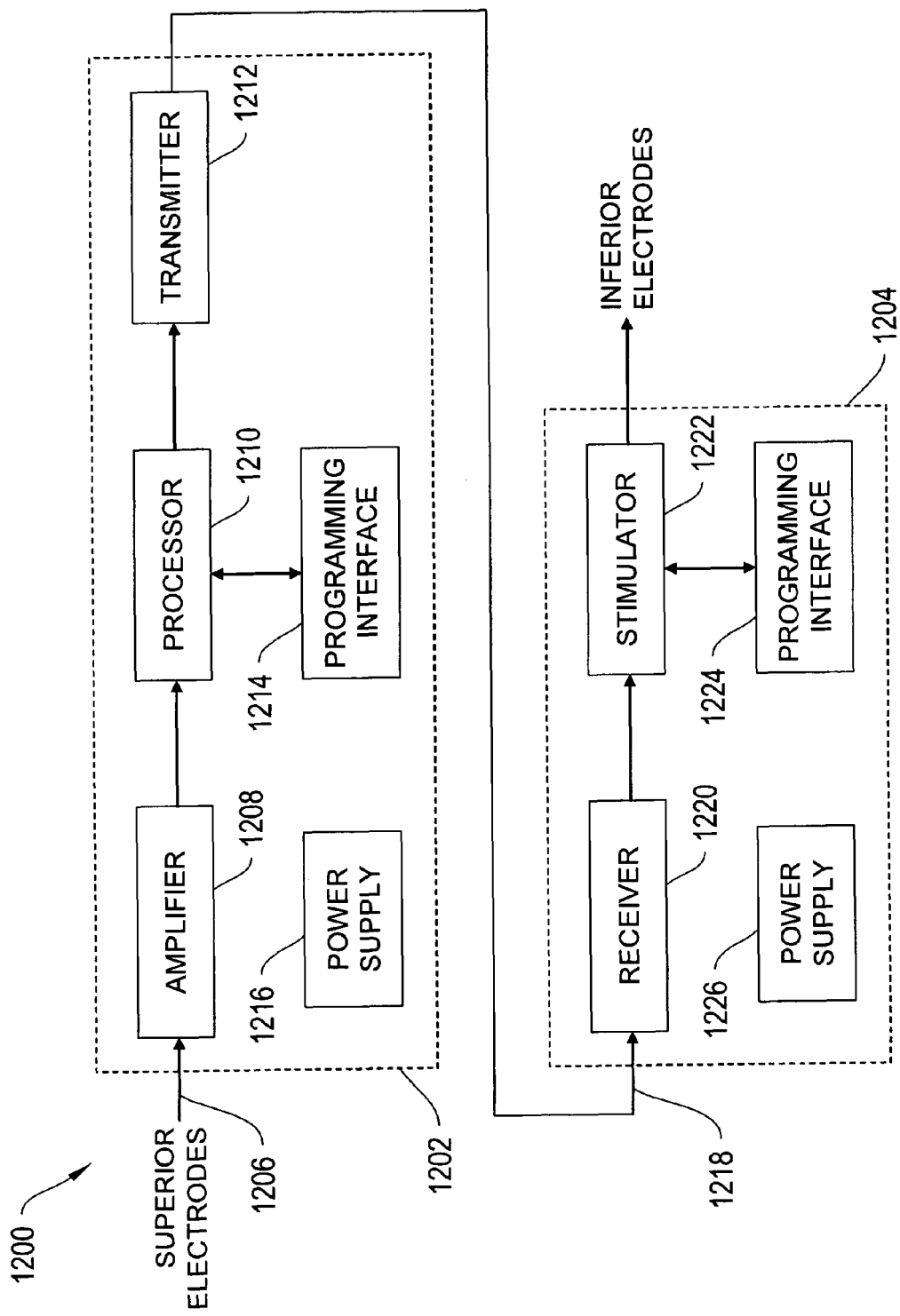
FIGS. 12 and 13 depict block diagrams for exemplary processing circuitry that may be used in a spinal cord transfer interface system, according to some aspects of the invention.
Figure 13:
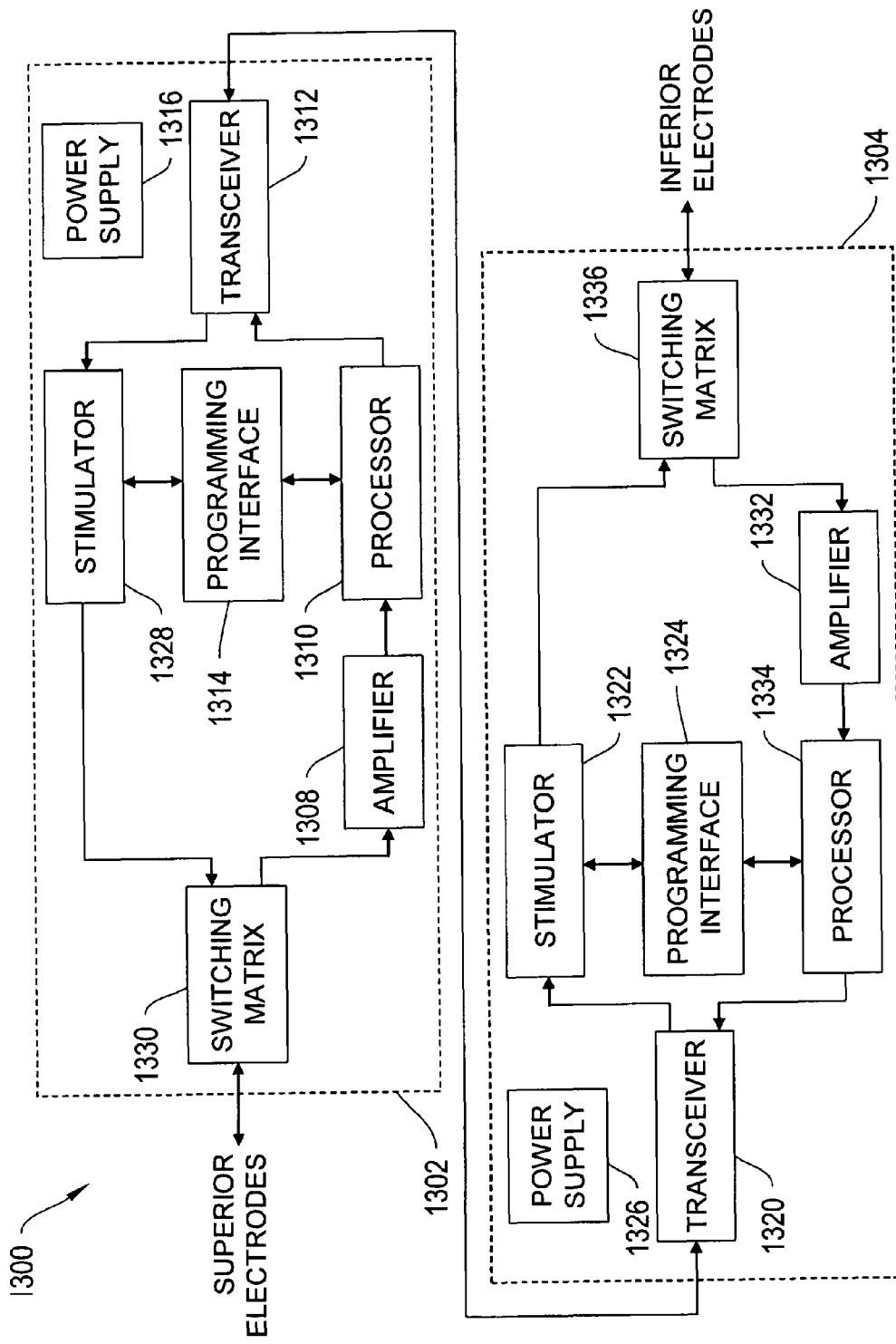

FIGS. 12 and 13 depict block diagrams for exemplary processing circuitry that may be used in a spinal cord transfer interface system, according to some aspects of the invention. FIG. 12 depicts a block diagram for exemplary processing circuitry 1200 capable of processing and transferring signals from superior electrodes, such as those in the superior electrode assemblies 102, 202, 302, and 402 described above, to inferior electrodes, such as those in the inferior electrode assemblies 104, 204, 304, and 404 described above. Exemplary processing circuitry 1300 of FIG. 13 may, in addition, process and transfer signals from the inferior electrodes to the superior electrodes.

The processing circuitry 1200 includes superior processing circuitry 1202, a portion of which may be implanted near the superior electrodes, and inferior processing circuitry 1204, a portion of which may be implanted near the inferior electrodes. The superior processing circuitry 1202 receives a signal 1206 from the superior electrodes and includes an amplifier 1208 for amplifying the received signal 1206, a signal processor 1210 for processing the signal output by the amplifier, and a transmitter 1212 for transmitting the signal output by the signal processor 1210 to the inferior processing circuitry 1204. The superior processing circuitry 1202 may include a programming interface 1214 for modifying the signal processor 1210 and a power supply 1216 for powering the circuitry 1202. The inferior processing circuitry 1204 receives a signal 1218 from the superior processing circuitry 1202 via a receiver 1220, which outputs the received signal 1218 to a stimulator 1222 for generating a signal to be transmitted via the inferior electrodes. The inferior processing circuitry 1204 may include a programming interface 1224 for modifying the stimulator 1222 and a power supply 1226 for powering the circuitry 1204. The programming interfaces 1214 and 1224 allow a user to alter how the processing circuitry 1200 transfers signals received at the superior electrodes to the inferior electrodes. Such altering may occur during a physical therapy session and in response to feedback from a patient in which the superior and inferior electrodes are implanted.

Turning to FIG. 13, the processing circuitry 1300 includes superior processing circuitry 1302, a portion of which may be implanted near the superior electrodes, and inferior processing circuitry 1304, a portion of which may be implanted near the inferior electrodes. The superior processing circuitry 1302 receives a signal from the superior electrodes and includes an amplifier 1308 for amplifying the received signal, a signal processor 1310 for processing the signal output by the amplifier, and a transceiver 1312 for transmitting the signal output by the signal processor 1310 to the inferior processing circuitry 1304. The transceiver 1312 may also receive signals from the inferior processing circuitry 1304 and transmit them to a stimulator 1328 for generating a signal to be transmitted via the superior electrodes. A programming interface 1314 may modify the signal processor 1310 and/or stimulator 1328, allowing a user to alter how the processing circuitry 1300 transfers signals between the superior and inferior electrodes. A switching matrix 1330, in communication with the superior electrodes, amplifier 1308, and stimulator 1328, determines whether the superior electrodes are receiving signals, which are transmitted to the amplifier 1308, or transmitting signals from the stimulator 1328. A power supply 1316 powers the superior processing circuitry 1302.

The inferior processing circuitry 1304 is similar to the superior processing circuitry 1302. A transceiver 1320 receives a signal from the superior processing circuitry 1302 and outputs the received signal to a stimulator 1322 for generating a signal to be transmitted via the inferior electrodes. The inferior processing circuitry 1304 may also receive signals from the inferior electrodes which are then amplified by an amplifier 1332, whose output signal is processed by a signal processor 1334 to generate a signal to transmit to the superior processing circuitry 1302 via the transceiver 1320. A programming interface 1324 may modify the stimulator 1322 and/or signal processor 1334, allowing a user to alter how the processing circuitry 1300 transfers signals between the superior and inferior electrodes. A switching matrix 1336, in communication with the inferior electrodes, amplifier 1332, and stimulator 1322, determines whether the inferior electrodes are receiving signals, which are transmitted to the amplifier 1332, or transmitting signals from the stimulator 1322. A power supply 1326 powers the inferior processing circuitry 1304.

Altering how the processing circuitry 1300 transfers signals via the programming interfaces 1314 and 1324 may occur during a physical therapy session and in response to feedback from a patient in which the superior and inferior electrodes are implanted. The transceivers 1312 and 1320 may transmit and receive signals via a wire or wirelessly.

Following implantation of electrode assemblies of a transfer interface in an injured spinal cord, processing circuitry of the electrode assemblies, such as processing circuitry 1200 and 1300 described above, may be programmed and/or altered to determine how signals will be transferred between superior and inferior electrodes of the transfer interface. The programming may occur over a number of physical therapy sessions with the patient, according to a predetermined procedure for evaluating electrodes and signals received or stimulated thereon. In some embodiments, a procedure first evaluates electrodes by determining which electrode contacts are functional and active, and then devises algorithms for translating recorded signals into stimulation signals corresponding to specific body movements. An exemplary procedure for electrode evaluation and algorithm programming follows:

I. Superior electrode assembly cord recording evaluation
   A. Evaluate each electrode for function
      i. Impedance testing
         a. Use the ground plane on the electrode array backing as the reference
         b. Evaluate each electrode by passing a 1 µA signal through it. (Note this signal may depend upon the electrode area and shape.)
            1. The electrode will be considered active if its impedance at 30 Hz, 250 Hz, and 1 KHz is within the design specifications of the electrode manufacturer.
            2. If the electrode impedance is outside of the operational range it will be conditioned using a conditioning pulse defined by the electrode manufacturer.
               a. The electrode will be tested again at the three impedance values.
               b. If the electrode remains outside of specifications it will be removed from the grid by setting a software flag to disable the switching matrix from activating this electrode.
         c. This impedance test will automatically be run at least once daily.
      ii. Recording field evaluation
         a. The patient will be asked to try to make specific movements in their lower extremities.
            1. Example Movements
               a. Each side separately
                  i. Dorsal Flexion
                  ii. Planter Flexion
                  iii. Wiggle the toes
                  iv. Knee Flexion
                  v. Knee Extension
                  vi. Hip Flexion
                  vii. Hip Extension
               b. Bilateral
                  i. Stand up on toes
                  ii. Roll over
                  iii. Sit up
                  iv. Walk
                  v. Jump
                  vi. Stand on one leg
                  vii. Stand on the other leg
                  viii. Sway back and forth
            2. For each movement, which will be evaluated 20 times for 5 consecutive days, the software will store the following from each electrode contact
               a. Rectified and integrated activity
                  i. Over the complete event
                  ii. Over short time intervals (e.g., 50 millisecond blocks)
               b. Firing rate (zero crossing)
                  i. Over the complete event
                  ii. Over short time intervals
               c. Spectral bands
                  i. Over the complete event
                  ii. Over short time intervals
            3. With the stored data the following analyses will be performed within each movement pattern and across each pattern to differentiate electrode activation patterns for each movement
- a. Cluster analysis
- b. Correlation analysis
- c. Spectral and cross-spectral analysis
- d. Bispectral analysis 4. Electrodes will be given a weighted score between zero and 100 for each test and evaluation. The goal is for the cluster analysis of the rectified and integrated data to be the primary measure for movement detection, although the frequency analysis may be used for determining walking.

iii. All analysis will be performed on an external computer and software that is connected to the patient via a wireless radio frequency transmitter/receiver system.

iv. Once all weightings have been established for each of the evaluations they will be downloaded to the on-board processor for real-time recording evaluation.

B. Inferior electrode assembly stimulation evaluation i. Impedance testing will be performed in a method similar to that described in I.a.i.2.

ii. This testing procedure will be performed in two phases. Phase I will evaluate each individual stimulating electrode. Phase II will evaluate groups of electrodes.

iii. For phase I, pairs of sterile needled electrodes or small surface gold cup electrodes will be placed in (or on the surface) of the leg muscle as follows:
- a. 1 pair in the Adductor Hallucis
- b. 1 pain in the Abductor digiti minimi
- c. 1 pair in the Flexor hallucis brevis
- d. 1 pair in the flexor digitorum brevis
- e. 1 pair in the abductor hallucis
- f. 2 pairs in the flexor hallucis longus
  1. 1 pair 3 cm distal to the center of the muscle
  2. 1 pair 3 cm proximal to the center of the muscle
- g. 1 pair in the flexor digitorum longus
- h. 1 pair in the soleus
- i. 1 pair in the lateral head of the gastrocnemius
- j. 1 pair in the medial head of the gastrocnemius
- k. 1 pair in the biceps femoris
- l. 1 pair in the semitendinosus
- m. 1 pair in the anterior tibialis
- n. 1 pair in the extensor digitorum brevis
- o. 1 pair in the vastus medialis
- p. 1 pair in the vastus lateralis
- q. 1 pair in the vastus intermedius
- r. 1 pair in each of the posterior spinal muscles below the level of the stimulation
- s. 1 pair in the gluteus maximus
- t. 1 pair in the rectus femoris
- u. 1 pair in the iliopsoas
- v. 1 pair in the adductor longus iv. Stimulation will then be done at a frequency of 2.4 Hz and a pulse width of 200 microseconds.

v. Amplitude will be slowly raised from 0 µA to 100 µA.
- a. The level of each EMG activation will be noted.
- b. Flags will be set in the software relating the level of stimulation and the muscle stimulated for each active contact.

II. Translation of data

A. The software will be programmed with the muscle and level table that was determined from the above tests.

i. The software will then be used to translate the recorded fields that were determined by looking at the weights of maximal activation with a desire to move.

ii. This will then activate the appropriate switching matrix on the stimulation side iii. Stimulation weights will then be applied by setting the appropriate current levels for stimulation at each switch iv. Stimulation will then be activated to move the appropriate muscle groups.

v. During the desire for more complex movements motor programs will be activated.

vi. These programs can be activated by:
- a. An external device the patient can use and control by hand
- b. A long term goal is to have the system automatically determine the activity via the recorded signals.

B. For safety purposes the system will have to evaluate external electrical influence and reject them—this will be part of an on board coil to pick up signals that are large and external and put the system in a safe mode.

III. A secondary goal is to have recording electrodes placed inferior to the injury site and stimulation electrodes placed superior to the injury site for sensation transfer A. If these secondary electrodes are added evaluation of the system will be performed as follows.

i. Sensations will be evaluated by testing each dermatomal level with
- a. Light touch—a brush
- b. Pressure
- c. Cold
- d. Heat
- e. Needle stick ii. Fields will be determined in a manner similar to the cranial electrode motor testing in part I.A.ii iii. Stimulation of each superior sensation electrode will be tested individually and the patient will respond by verbalizing what they feel.

Described herein are exemplary embodiments of the invention that are presented for purposes of illustration and not of limitation. Applicants consider all operable combinations of the embodiments disclosed herein to be patentable subject matter.

The invention claimed is:

1. A method of restoring or enhancing motor function to a patient with a spinal cord injury, the method comprising:
receiving signals originating in at least one of a brain and a central nervous system of the patient at a superior electrode array implanted in the spinal cord superior to the spinal cord injury;
transmitting signals from the superior electrode array to an inferior electrode array implanted in the spinal cord inferior to the spinal cord injury in response to the nervous signals;
receiving the transmitted signals with the inferior electrode array; and
stimulating the spinal cord in response to the received signals to restore or enhance motor function of the patient.

2. The method of claim 1 wherein transmitting signals includes wirelessly transmitting signals from the superior electrode array to the inferior electrode array.

3. The method of claim 1 further including:
generating stimulation signals in response to the received signals; and
wherein stimulating the spinal cord includes applying the stimulation signals to the spinal cord with inferior electrode array.

4. The method of claim 1 wherein transmitting the signals from the superior electrode array to an inferior electrode array includes:
transmitting the signals to an external processor;
altering the signals with the external processor based on a desired motor function response; and transmitting the altered signals from the processor to the inferior electrode array.

5. The method of claim 1 further comprising:
receiving other signals originating in a peripheral nervous system of the patient at the inferior electrode array; and
transmitting the other signals from the inferior electrode array to the superior electrode array.

6. The method of claim 1 further comprising:
evaluating which electrodes in the superior and inferior electrode arrays are functional; and
translating recorded signals into stimulation signals corresponding to specific body movements based on the evaluation.

7. The method of claim 1 further comprising:
implanting processing circuitry within a subdural space of the spinal cord; and
coupling the processing circuitry to at least one of the superior and inferior electrode arrays.

8. A method for treating a patient with a spinal cord injury, the method comprising:
  (a) implanting a superior electrode array in a spinal cord superior to a spinal cord injury site;
  (b) implanting an inferior electrode array in the spinal cord inferior to the spinal cord injury site;
  (c) evaluating which electrodes in the superior and inferior electrode arrays are functional; and
  (d) placing the superior electrode array in electrical communication with the inferior electrode array.

9. The method of claim 8 wherein implanting at least one of the superior and inferior electrode arrays includes positioning the at least one of the superior and inferior electrode arrays within a subdural space of the spinal cord.

10. The method of claim 9 wherein implanting at least one of the superior and inferior electrode array includes:
removing a lamina of a vertebra; and
opening a dura mater to expose a subdural space.

11. The method of claim 8 wherein implanting at least one of the superior and inferior electrode arrays includes positioning the at least one of the superior and inferior electrode arrays along a lateral side of the spinal cord.

12. The method of claim 8 wherein implanting the superior electrode array includes positioning the superior electrode array along a lateral side of the spinal cord and further comprising:
implanting another superior electrode array along another lateral side of the spinal cord.

13. The method of claim 8 wherein implanting at least one of the superior and inferior electrode arrays includes positioning the at least one of the superior and inferior electrode arrays along a dorsal side of the spinal cord.

* * * * *